United States Patent [19]

Ehrhardt

[11] 4,344,446

[45] Aug. 17, 1982

[54] COMBINED SCALP AND HAIR CARE PRODUCTS AND METHOD

[75] Inventor: Horst Ehrhardt, Canoga Park, Calif.

[73] Assignees: Susan Bjurman; Barbara Babcock, both of Los Angeles, Calif.

[21] Appl. No.: 131,274

[22] Filed: Mar. 17, 1980

[51] Int. Cl.³ .............................................. A45D 7/00
[52] U.S. Cl. .......................................... 132/7; 424/70
[58] Field of Search ........................ 132/7; 424/70–71, 424/78

[56] References Cited

U.S. PATENT DOCUMENTS

| | | | |
|---|---|---|---|
| 3,810,478 | 5/1974 | Olson | 132/7 |
| 4,047,537 | 9/1977 | Shaw | 132/7 |
| 4,061,150 | 12/1977 | Dasher | 132/7 |
| 4,263,178 | 4/1981 | Guth | 132/7 |

Primary Examiner—G. E. McNeill
Attorney, Agent, or Firm—Sherman & Shalloway

[57] ABSTRACT

A total head care package of a solid stick-like scalp cleanser and a cleaning and conditioning hair shampoo is provided along with a method of cleansing the scalp and cleaning and conditioning the hair.

The solid scalp cleanser is a substantially anhydrous formulation which includes soap, amphoteric detergent and antimicrobial agent in a wax-like base.

The hair shampoo both cleans and conditions the hair and includes a cationic salt of a primary aliphatic amine with amphoteric detergents. The hair shampoo is typically in the form of a gel. The cationic salt increases strength and stretchability of the hair shafts and reduces static charge buildup.

The solid scalp cleanser which may be molded into a lipstick configuration is first applied to the scalp and, before the scalp cleanser is removed the hair shampoo is applied. Both products are then removed by rinsing.

4 Claims, No Drawings

COMBINED SCALP AND HAIR CARE PRODUCTS AND METHOD

BACKGROUND OF THE INVENTION

Field of the Invention

This invention relates to compositions and method for cleansing and conditioning the hair and scalp. More particularly the invention relates to a total scalp and hair care product of a conditioning and cleansing shampoo with a solid stick for cleansing the scalp and to a method using the total scalp and hair care product.

Background of the Invention

In recent years many liquid and gel shampoo formulations have been described in the literature and have become commercially available which are designed to provide both a cleansing and conditioning treatment to the hair. These are stated to be an improvement over the many commercially available conditioning creme rinse formulations which are applied to the hair after a previously applied cleansing shampoo has been thoroughly rinsed from the hair.

Whether in a combined cleanser/conditioner or separate cleanser shampoo/conditioner rinse the prior art has concentrated on alleviating some of the undesirable effects of synthetic detergents used in hair treatment formulations. These undesirable effects include, for example, unmanageability, stickiness, static buildup, stringiness and similar problems. It is generally believed that the removal of natural oils, lipids, sebum and other natural components on and of the hair and scalp during the shampooing process is responsible for these undesirable effects.

Nevertheless, little or no serious attention has been given to formulations designed especially for cleansing the scalp—in contrast to cleansing the scalp hair—so that a subsequently used liquid hair shampoo might provide its cleansing and conditioning functions without undesirable side effects due to removal of desirable components of the hair and scalp or other causes.

It is, therefore, an object of the invention to provide a convenient to use total head care package which includes solid scalp treatment composition which can be used alone or in conjunction with a hair cleansing and conditioning shampoo.

It is a further object to provide a hair cleansing and conditioning shampoo which is not only effective in cleaning dirty hair but also in conditioning and treating healthy as well as damaged hair.

It is another object of the invention to provide a stick-like solid scalp cleansing composition which is easy to apply to the scalp without adversely effecting the hair.

A further object of the invention is to provide a method for cleansing the scalp and cleaning and conditioning the hair in which the scalp treatment does not adversely affect the hair and the hair treatment does not adversely affect the scalp.

Still other objects and advantages of the invention will become clear from the following summary and detailed description of the invention.

SUMMARY OF THE INVENTION

The total head care package of the invention includes a stick-like waxy solid scalp treating composition containing an alkali metal fatty acid soap, an alcohol-propylene glycol solvent humectant base, a non-irritating amphoteric surfactant, an antimicrobial agent and an emulsifier for providing a stable solid waxy composition and by a hair cleansing and conditioning shampoo containing a mixture of at least one amphoteric detergent and a cationic salt of a dibasic acid with a primary amine. The shampoo may also include other synthetic detergents including a minor amount of anionic detergents and conditioning agents including nonionic super amide polymers, cationic proteins, bacteriocides, fragrances and other conventional shampoo additives.

According to the method of treating the scalp and hair the stick-like scalp cleanser is first applied to the scalp while avoiding as much as possible contacting the hair. With the scalp cleanser still in place the hair is shampooed. The scalp cleanser and shampoo are then thoroughly rinsed with water and the hair dried as with conventional shampoos. The hair should be wetted prior to applying the scalp cleanser although this is not absolutely necessary. However, since the hair must be wet before applying the shampoo it is most convenient to wet the hair before applying the scalp cleanser.

DETAILED DESCRIPTION OF THE INVENTION

The solid waxy scalp cleansing composition includes an alkali metal soap of a fatty acid for its cleansing action. Examples of suitable soaps include sodium and potassium salts of fatty acids of from about 10 to about 24 carbon atoms, preferably from about 12 to about 20 carbon atoms. Examples of the fatty acids include stearic acid, lauric acid, myristic acid, palmitic acid, oleic acid, hydrogenated and non-hydrogenated coconut oil or tallow fatty acids and the like.

The soap component can be formed in the presence of the other ingredients by reacting the fatty acid and sodium or potassium hydroxide in situ at a concentration of from about 8 to about 13% by weight of the total composition. The reaction should be carried out at a relatively low alkaline pH of about 7.1 to about 8.5 in a humectant base of propylene glycol for example, with an alcohol solvent. The proportion of the glycol and alcohol may vary from about 5:1 to about 1:5, preferably about 4:1 to about 1:4, by weight. The glycol component will be the major solvent for dry scalp while the alcohol will predominate for oily scalp. For normal hair relatively equal proportions can be used.

A second essential ingredient of the scalp cleanser is a betaine, especially of the cocoamido alkyl betaine type. The betaine detergent should be present in an amount of from about 3% to about 8% by weight of the composition. This ingredient provides some antimicrobial activity in addition to its cleaning activity. The betaines are also advantageous because they are non-irritating to the skin or to the eyes.

Betaine type detergents are generally well known in the art and can be represented by the following general structure:

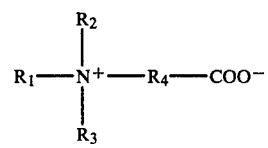

wherein $R_1$ is an alkyl group containing about 8 to 18 carbon atoms; $R_2$ and $R_3$ are lower alkyl or hydroxyalkyl groups containing about 1 to 3 carbon atoms and $R_4$ is an alkylene or hydroxy-alkylene group containing about 1 to 4 carbon atoms. Examples of the betaine in addition to the preferred cocoamido alkyl betaine, which is commercially available under the trademark Tego Betaine-C, include, for example, 1-(myristyl dimethyl ammonium)acetate, N-heptadecyl-N, N-bishydroxyethylaminoacetate, etc.

An antimicrobial or fungicidal agent is also included in the scalp cleanser formulation. As examples of the antimicrobial or fungicidal agent mention may be made of Ottasept, Methyl and Ethyl Parasept, etc.

Ottasept is a trademark of Ottawa Chemical Company for p-chloro-m-xylenol and 4-chloro-2,6-xylenol. Parasept is a trademark of Heyden Newport Chemical Corporation for a line of parahydroxybenzoates including methyl $[C_6H_4(OH)COOCH_3]$ and propyl $[C_6H_4(OH)COOC_3H_7]$ compounds. Any other non-toxic germicide including microbicides, bactericides or fungicides which are well known in the art can also be included in the scalp cleansing formulation. The amount of this ingredient need only be that amount which is germicidally effective.

Another essential ingredient in the scalp cleanser formulation is the emulsifier which provides the necessary consistency and stability to the stick compositions. The preferred class of emulsifiers are the solid wax-like polyoxyethylene fatty alcohol ethers such as the Promulgen emulsifiers or the high molecular weight fatty acid mono- or di-esters of high molecular weight polyethylene glycol, such as a mono- or di-ester of polyethylene glycol, such as a mono- or di-ester of polyethylene glycol 6000 with a higher fatty acid having from about 6 to about 33 carbon atoms.

The waxy emulsifier is used in an amount of from about 0.5 to about 3.0% by weight of the total composition. In addition to stabilizing the solid stick, the waxy emulsifier also enhances the ease in applying the solid stick to the scalp.

Other additives which can be included in the scalp cleanser include scalp conditioning agents, fragrances, pigments, dyes and the like.

A particularly effective class of additives for treating dry scalp is the dialkyl esters of lower aliphatic dicarboxylic acids of from 3 to 8 carbon atoms, for example adipic acid, glutaric acid, succinic acid, 3,3-dimethyl-pentanedioic acid, and the like. The alkyl groups preferably have from about 2 to about 6 carbon atoms. The preferred dry scalp conditioning additive is diisopropyl adipate. The amount of the additive is generally from about 5 to about 10% by weight of the composition for dry scalp cleansing formulations and from about 0 to about 5% by weight for oily or normal scalp cleansing formulations. The dry scalp additive can be entirely omitted from oily and normal formulations.

The solid stick scalp cleansing composition can be simply prepared by adding all of the ingredients except the alkali metal hydroxide and fatty acid to the propylene glycol humectant-solvent at room temperature, mixing to a uniform consistency, heating the mixture to an elevated temperature; for example 100° C. to 200° C., preferably about 160° C., until the viscosity of the mixture becomes sufficiently thin. The alkali ingredient, e.g. NaOH is poured into the heated mixture and then, preferably with mixing, the fatty acid, e.g. stearic acid, is slowly added to the heated mixture until the pH of the mixture reaches about 8.3 in the case of stearic acid. It has been found that at pH values below about 8.3 the stick may be too soft while at pH values above about 8.3 the color and stability of the stick becomes degraded. The optimum pH can readily be determined for other forms of soap and other combinations of ingredients. After the fatty acid has been added the heated mixture is placed into a mold and allowed to cool. Generally, about 30 minutes is sufficient for the mixture to cool to a sufficiently firm form. The cooled mixture will be substantially clear and transparent although as noted above dyes and/or pigments can be added as desired.

The degree of hardness of the stick will generally be determined by the amount of the soap ingredient included in the formulation, the higher the amount of soap the harder the formulation.

The liquid hair cleansing and conditioning shampoo includes a unique blend of detergent and conditioning ingredients which are capable of increasing the strength and stretchability of the hair shaft and to diminish static buildup. These effects are even noticeable when the shampoo is applied to damaged hair.

The principal detergent component is an amphoteric imidazoline detergent. Examples of the imidazoline detergents include the long chain imidazole derivatives such as those sold under the tradename "Miranol" and having the formula:

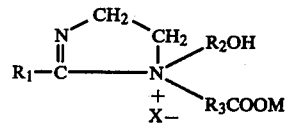

wherein $R_1$ is an alkyl group of about 10 to 20 carbon atoms, $R_2$ and $R_3$ are independently an alkylene or hydroxyalkylene group containing 1 to 4 carbon atoms, M is a water soluble cation, e.g. alkali metal, ammonium, mono-, di-, or tri-alkylolammonium, etc., and X is a water soluble anion, e.g. hydroxyl, chloride, sulfate, acetate, etc. The "Miranols" are generally described in U.S. Pat. Nos. 2,528,378 and 2,781,354. Other suitable amphoteric imidazole detergents include compounds of the formula:

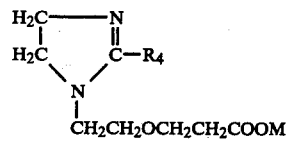

wherein $R_4$ is a higher acyclic group of 7 to 17 carbon atoms and M is a water-soluble cation. These compounds are described in U.S. Pat. No. 2,267,965. In the above formula $R_1$ may typically be derived from coconut oil fatty acids; lauric fatty acid, andoleic fatty acid, with alkyl groups being the preferred acyclic groups.

The amphoteric imidazoline detergents which are useful in the shampoo formulations of this invention are non-irritating to the human eye. The amount of the imidazoline detergent compound can range from about 3 to about 20% by weight, preferably from about 4 to 10% by weight of the total composition.

In conjunction with the amphoteric detergent base a cationic salt of a primary amine of the structure:

were R represents a straight or branched chain aliphatic hydrocarbon chain containing from 8 to 22 carbon atoms, reacted with a dibasic acid of the structure:

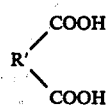

wherein R' represents an aliphatic chain containing from 1 to 6 carbon atoms, is used in an amount of from about 3 to about 20% by weight, preferably from about 4 to 10% by weight of the total composition.

Exemplary of these cationic diacid salts mention can be made of cationic salts of dicarboxylic acid monoesters. Suitable dibasic or dicarboxylic acids include malonic acid, succinic acid, glutaric acid and adipic acid. Suitable primary amines include, for example, oleylamine, N-octyldecylamine, N-stearylamine, isododecylamine and the like.

The cationic salts are prepared by simply mixing together the dibasic acid with the primary amine and heating the mixture to melt the reactants and allow the salt to form. Upon cooling the salt crystallizes to a solid particulate form. The heating/reaction temperature should not be so high as to convert the amine to an amide. In the case where the dibasic acid is adipic acid and the fatty amine is oleylamine the maximum heating temperature is about 70° C.

These cationic salts impart superior conditioning properties to the shampoo and in particular strengthen the hair and impart stretchability to the hair, especially the hair shafts which are most susceptible to damage.

Other conventional shampoo conditioning and cleansing agents and adjuvants can also be included in the shampoo. For example, mention can be made of nonionic superamides for foam and cleansing boosting action, the nonionic form being necessary to prevent interaction with the cationic salt. An example of the superamide is Henkel LD 80/20, a modified lauric-myristic diethanolamide. Similarly, proteins for strengthening the hair can be included and should also be in the cationic form to prevent interaction with the cationic salts. Quaternized proteins such as Crotien BTA of the Croda Chemical Company are especially preferred. Other conventional conditioning agents, such as Jojoba oil, D-panthenol, lecithins, etc. nonionic surface active agents and adjuvants such as thickening agents, preservatives, pH modifying agents, coloring agents, fragrances, solvents and the like, in minor amounts to give their desired effect without adversely effecting the amphoteric detergents and cationic salts can also be included.

The shampoo can be prepared by adding all of the ingredients, except the cationic salt, to water, or other aqueous solvent, such as water-alcohol mixtures. Small amounts of anionic surfactants, such as ammonium lauryl sulfate can also be included in the shampoo. It has been found that amounts of the anionic surfactant of less than about 5% by weight, especially less than 3% by weight, of the total formula, aids in the formation of the shampoo into a stable gel but does not disrupt the action of the cationic salt.

After all of the ingredients, except the cationic salt, are added to the aqueous solvent, the mixture is heated and the cationic salt is added slowly, as the mixture forms a very thick heavy flowing gel. The pH of the formulation can be adjusted with, for example, lactic acid, to a pH of about 7 or less, preferably about 4 to about 6.5, especially about 4.5 to 5.8, since the gels tend to be more stable at the slightly acidic pH's.

For ease of application the solid stick scalp cleanser can be molded into the shape of a pencil or lipstick. Other forms such as those associated with stick deodorants which are generally rectangular or oval in cross-section, or a generally cylindrical body with a widened fan-shaped head would also be suitable and would provide additional surface area to shorten the time for application to the scalp.

In use, the hair is first wetted and the scalp cleaner is rubbed on the scalp. The consistency of the stick will be such that only a light pressure is necessary to apply a suitable small amount of the cleanser composition to the scalp. The massaging of the scalp cleanser to the scalp can be accomplished in a short period of time, for example, about 1 or 2 minutes.

After massaging in the scalp cleanser, the hair is shampooed as follows: work shampoo into creamy lather, and smooth on hair to ends. Optionally, a large tooth comb can be used to work shampoo to hair ends. After shampooing, the hair and scalp are then thoroughly rinsed with water to wash away the scalp cleanser and hair shampoo. The procedure can be repeated if necessary, but it is an advantage of the total head care treatment products of this invention that a second application is not particularly necessary. This is in contrast to most hair shampoos which recommend repeated washing of the hair.

It can therefore be appreciated that the present invention provides a unique head care treatment program wherein cleaning and conditioning agents designed for treatment of the hair are not brought into contact with the scalp where they could have a damaging effect and similarly cleansing agents and conditioning agents and germicides designed for treatment of the scalp can be eliminated from contact with the hair. Thus, only the beneficial effects without the potentially damaging effects to the scalp and hair can be easily achieved.

The invention will now be described in greater detail by way of specific, non-limiting examples of the scalp cleansing compositions, and the cleaning and conditioning hair shampoo gel. In the examples all parts and percents are on a weight basis unless otherwise noted.

Example 1. Stick-like Scalp Cleanser

The following formulation is used:

|  | Dry | Normal | Oily |
|---|---|---|---|
| Propylene Glycol (humectant base) | 45–65% (50–55) | 30–35 | 45–65% (14–16) |
| SDA 40 alcohol (solvent) | 10–20% (14–16) | 20–35 | 10–20% (50–55) |
| Stearic Acid (soap) | 6–12% (8–10) | 12 | 6–12% (8–10) |
| 50% sodium hydroxide (soap) | 2.0–3.5% (2.4–3.0) | 3 | 2.0–3.5% (2.4–3.0) |
| Diisopropyl adipate (conditioner) | 5–10% (6–8) | 2 | <1% (0) |
| Cocoamido alkyl hetaine (detergent) | 3.0–5.0% (3.6–4.4) | 3.6–4.4 | 3.0–5.0% (3.6–4.4) |

-continued

| | Dry | Normal | Oily |
|---|---|---|---|
| Ottasept (antimicrobial) | 0.1–0.4% (0.2–0.3) | .2–.3 | 0.1–0.4% (0.2–0.3) |
| Promulgen G (emulsifier) | 3.0–7.0% (4.0–6.0) | 4–6 | 3.0–7.0% (4.0–6.0) |
| Fragrance | .20–.40% (.25–.35) | .25–.35 | .20–.40% (.25–.35) |

NOTE:
Numbers in parenthesis represent preferred ranges of all ingredients.

All of the ingredients, except the stearic acid and the sodium hydroxide are added to the propylene glycol and alcohol and mixed in a beaker with a magnetic stirrer. The mixture is heated to about 160° C. and maintained at this temperature in a heated bath. While continuing to stir the NaOH is added to the beaker and the stearic acid is then slowly poured into the beaker until the pH reaches 8.3 when the soap forming reaction is completed.

While still hot the mixture is poured into a cylindrical mold about one-half inch in diameter with a rounded bottom. The mixture is allowed to cool and is removed from the mold after 30 minutes. The resulting lipstick like product is clear and has a waxy feel.

Example 2. Cleansing and Conditioning Shampoo Gel

The cationic salt is first formed by reacting about 4.1 parts Kemamine, an oleyl amine, which is a product of Humble with about 2.3 parts adipic acid. The two ingredients are heated to about 68° to 70° C. to complete the salt forming reaction. The resulting cationic salt is allowed to cool and solidify.

The shampoo is formed by adding the amphoteric detergents, cationic salt, and other additives, in the proportions shown below, to water, and mixing until clear at room temperature.

| | Dry | Normal | Oily |
|---|---|---|---|
| Water | 35–55 | 35–55 | 35–55 |
| Cationic Salt | .5–2 (1) | .5–2 (1.0) | .5–2 (1.0) |
| Amphoteric dicarboxylic coconut derivative of ethanolamine salt (Miranol) (salt-free Henkel 9-F-15934 | 10–20 (15) | 10–20 (15) | 10–20 (15) |
| Cocoamidopropylbetaine (carsonam 3147) | 15–30 (25) | 15–30 (25) | 15–30 (25) |
| Lauryl dimethyl amine oxide (carsonam 32-228) | .5–2 (1) | .5–2 (1) | .5–2 (1) |
| Jojoba Oil or Diadipate | 2 | 1 | 0 |
| 2-Isoheptadecyl-1-Hydroxyethyl Propanoic Acid Imidazoline (Mona Isoteric 35) | 2–7 (5) | 2–7 (5) | 2–7 (5) |
| Ammonium Lauryl Sulfate | 3–6 (4) | 3–6 (4) | 3–6 (4) |
| Lactic Acid or Phosphoric Acid | To pH of 4.7–5.4 | | |
| Fragrance | .25 | .25 | (5.2) .25 |
| Cocosuperamide (Emery 6514) | 2–5 | 2–5 | 2–5 |
| Quaternized Protein (Crotien B.T.A.) | 3 | 2 | 1 |
| Aloe Vera | .2–.5 | .2–.5 | .2–.5 |
| Dipanthenol | .2–.5 | .2–.5 | .2–.5 |
| Perservative | .2–.5 | .2–.5 | .2–.5 |

The pH must first be brought to the range of from 4.7 to 5.2 before adding the ammonium lauryl sulfate.

While the solid waxy stick-like scalp cleanser and cleaning and conditioning gel shampoo are formulated to complement each other it should also be understood that various modifications of each of the formulations can be made without departing from the scope and spirit of the invention. For example, the shampoo can be in the form of an easily flowing liquid rather than a heavy flowing gel. It should also be understood that while the scalp cleanser and hair shampoo are designed to be used in conjunction with each other, each can be used separately and still give superior head care treatment.

What is claimed is:

1. A total hair care product for cleansing the scalp and cleansing and conditioning the hair, said product comprising:
   (A) a solid waxy stick-like scalp cleanser comprising alkali metal fatty acid soap, amphoteric detergent, antimicrobial agent and emulsifier in a substantially anhydrous humectant solvent; and
   (B) a cleaning and conditioning hair shampoo aqueous gel comprising a cationic amine salt which is the reaction product of a primary amine of the formula $RNH_2$ where R represents an aliphatic hydrocarbon chain containing from 8 to 22 carbon atoms with a dicarboxylic acid of the formula $HOOC—R'—COOH$ where R' represents an aliphatic hydrocarbon containing from 1 to 6 carbon atoms, and at least one amphoteric detergent.

2. A solid waxy stick-like scalp cleanser comprising alkali metal fatty acid soap, amphoteric detergent, antimicrobial agent and emulsifier in a substantially anhydrous humectant solvent.

3. A cleaning and conditioning hair shampoo aqueous gel comprising a cationic amine salt which is the reaction product of a primary amine of the formula $RNH_2$ where R represents an aliphatic hydrocarbon containing from 8 to 22 carbon atoms with a dicarboxylic acid of the formula $HOOC—R'—COOH$ where R' represents an aliphatic hydrocarbon containing from 1 to 6 carbon atoms, and at least one amphoteric detergent.

4. A method of total head care treatment for cleaning and conditioning both the scalp and hair comprising contacting the scalp with a waxy, solid stick-like applicator comprising an alkali metal fatty acid soap, amphoteric detergent, antimicrobial agent and emulsifier in a substantially anhydrous humectant solvent; thereafter cleaning and conditioning the hair with an aqueous shampoo composition comprising at least one amphoteric detergent and a cationic amine salt which is the reaction product of an aliphatic hydrocarbon chain containing from 8 to 22 carbon atoms with a dicarboxylic acid of the formula $HOOC—R'—COOH$ where R' represents an aliphatic hydrocarbon containing from 1 to 6 carbon atoms, and at least on amphoteric detergent.

* * * * *